United States Patent [19]

Imai et al.

[11] Patent Number: 4,788,371

[45] Date of Patent: Nov. 29, 1988

[54] CATALYTIC OXIDATIVE STEAM DEHYDROGENATION PROCESS

[75] Inventors: Tamotsu Imai; Deng-Yang Jan, both of Mt. Prospect, Ill.

[73] Assignee: UOP Inc., Des Plaines, Ill.

[21] Appl. No.: 139,690

[22] Filed: Dec. 30, 1987

[51] Int. Cl.$^4$ .......................... C07C 4/02; C07C 5/09; C07C 5/333

[52] U.S. Cl. .................................. 585/443; 585/444; 585/621; 585/624; 585/658

[58] Field of Search ............... 585/443, 444, 621, 624, 585/658

[56] References Cited

U.S. PATENT DOCUMENTS

| | | | |
|---|---|---|---|
| 3,502,737 | 3/1970 | Ghublikian | 260/669 |
| 3,670,044 | 6/1972 | Drehman et al. | 260/683.3 |
| 4,070,413 | 1/1978 | Imai | 260/683.3 |
| 4,180,690 | 12/1979 | Imai | 585/443 |
| 4,341,912 | 7/1982 | Takahashi et al. | 585/443 |
| 4,418,237 | 11/1983 | Imai | 585/443 |
| 4,435,607 | 3/1984 | Imai | 585/443 |
| 4,565,898 | 1/1986 | O'Hara et al. | 585/441 |
| 4,613,715 | 9/1986 | Haskell | 585/412 |
| 4,672,146 | 6/1987 | Abrevaya et al. | 585/660 |

*Primary Examiner*—Curtis R. Davis
*Attorney, Agent, or Firm*—Thomas K. McBride; John F. Spears, Jr.; A. Blair Hughes

[57] ABSTRACT

A novel process is disclosed for the steam dehydrogenation of dehydrogenatable hydrocarbons in the vapor phase in conjunction with oxidative reheating of the intermediate products. The process utilizes a single catalyst to perform both the selective oxidation and steam dehydrogenation functions. The particular catalyst employed comprises a Group VIII noble metal component, a Group IA and/or a Group IIA component and may contain among other modifiers a Group IIIA or IVA metal, and a halogen component. The catalytic components are supported on an inorganic substrate such as alumina.

24 Claims, 1 Drawing Sheet

CATALYTIC OXIDATIVE STEAM DEHYDROGENATION PROCESS

BACKGROUND OF THE INVENTION

This invention relates to a process for the conversion of hydrocarbons, and especially the dehydrogenation of dehydrogenatable hydrocarbons in the presence of a selective oxidation/dehydrogenation catalyst where steam and an oxygen-containing gas are co-feeds.

The dehydrogenation of hydrocarbons is an important commercial process. This is because of the great demand for dehydrogenated hydrocarbons as feedstocks for industrial processes. For example, dehydrogenated hydrocarbons are utilized in the manufacture of various products such as detergents, high octane gasolines, and pharmaceutical products among others. Plastics and synthetic rubbers are other products which may be produced through use of dehydrogenated hydrocarbons. One example of a specific dehydrogenation process is dehydrogenating isobutane to produce isobutylene which may then be polymerized to provide tackifying agents for adhesives, viscosity-index additives for motor oils and impactresistant and anti-oxidant additives for plastics.

INFORMATION DISCLOSURE

The prior art recognizes numerous hydrocarbon conversion processes which utilize a single catalyst to perform dehydrogenation and selective oxidation functions. The catalysts disclosed as being useful in such a process cover a wide range of compositions. Catalysts which are comprised primarily of metal oxides comprise one group of catalysts useful in a selective oxidation/dehydrogenation process. U.S. Pat. No. 3,502,737 (Ghublikian) discloses the use of an iron oxide catalyst in a process to dehydrogenate ethylbenzene into styrene and also to selectively oxidize hydrogen produced in the dehydrogenation reaction. U.S. Pat. No. 4,180,690 (Imai) discloses the use of a silica-based catalyst containing oxides of cobalt, chromium, aluminum, and magnesium for the oxydehydrogenation of an alkylaromatic. The processes disclosed in these and other prior art cases are similar to that of the instant invention except that the instant catalyst is comprised of a metal modified refractory oxide support as opposed to a metal oxide based catalyst.

U.S. Pat. No. 4,613,715 (Haskell) discloses a dehydrocyclization process employing a catalyst containing a Group VIII metal and at least one support material selected from the group consisting of Group IIA and Group IIB metal aluminate spinels. In the '715 process, free oxygen-containing gas is injected into the reaction mixture at at least one point downstream from where the hydrocarbon feed contacts the catalyst bed. The dehydrocyclization reaction is a two-step reaction which comprises dehydrogenation and olefin cyclization. The hydrocarbon conversion process of the instant invention is similar to that of the '715 patent. However, the catalyst disclosed in the '715 patent is a Group VIII metal on a Group IIA or IIB metal aluminate spinel whereas the catalyst of the instant invention is comprised of a Group VIII metal and a Group IA component on a refractory inorganic oxide support. The refractory inorganic oxide support is distinguished from the metal aluminate spinel in that the metal aluminate spinel is catalytically active whereas the refractory oxide support is catalytically inactive.

U.S. Pat. No. 3,670,044 (Drehman et al) describes a process for dehydrogenating dehydrogenatable hydrocarbons in the presence of oxygen and in the presence of a catalyst comprising Group II aluminate spinels, and a metal component selected from Group VIII metals. The process of the '044 patent can be distinguished from that of the instant invention on the basis of catalyst composition. Like the catalyst used in the process of the '715 patent, the catalyst utilized in the process of the '044 patent contains a Group II aluminate spinel. The distinguishing features between the Group II aluminate spinel and the refractory inorganic oxide support of the catalyst of the instant invention mentioned in the preceding paragraph also apply here. In addition, the catalyst of the instant process, unlike that of the catalyst of the process of the '044 patent is comprised of a Group IA component.

U.S. Pat. No. 4,672,146 (Abrevaya et al) describes a process utilizing a catalytic composite useful for the dehydrogenation of dehydrogenatable hydrocarbons. The catalyst contains, among other components, a Group VIII noble metal and an alkali metal component on an alumina support. This catalyst composition is similar to that of the present invention. However, from a process standpoint, the '146 patent fails to mention the utility of such a catalyst in the selective oxidation of hydrogen in the presence of oxygen at oxidation conditions. In fact, the '146 patent states a diluent may be introduced into the dehydrogenation process, but it mentions only hydrogen, steam, methane, ethane, carbon dioxide, nitrogen, and argon, and specifically hydrogen as the diluent. Oxygen addition as a process co-feed or diluent is never mentioned in the '146 patent, but it is a very important co-feed to the process of the instant invention.

U.S. Pat. No. 4,070,413 (Imai) likewise describes a paraffin dehydrogenation process employing a catalyst comprising a Group VIII metal component and an alkali metal component on an alumina support similar to the catalyst of the process of the present invention. Again however, the process described in the '413 patent is silent to the fact that the claimed catalyst is useful for selective oxidation in the same process. In fact, the '413 patent is silent as to the addition of any co-feeds or diluents besides hydrogen.

U.S. Pat. No. 4,435,607 (Imai) describes a process for the dehydrogenation of a dehydrogenatable hydrocarbon which employs a dehydrogenation catalyst and a different selective oxidation catalyst. The selective oxidation catalyst is comprised of a Group VIII noble metal, a Group IVA metal, and a Group IA or IIA metal on a highly porous alumina support. The oxidation catalyst of the '607 patent is similar in composition to that of the oxidation/dehydrogenation catalyst of the instant invention. The '607 patent however does not recognize the oxidation catalyst disclosed therein as a potential dehydrogenation catalyst and in fact claims the use of an alkaline metal-promoted iron compound as the dehydrogenation catalyst. The '607 patent is therefore silent to the benefits enjoyed in a process using a single catalyst to perform both oxidation and dehydrogenation functions.

Two other U.S. Pat. Nos. 4,565,898 (O'Hara et al) and 4,418,237 (Imai), similarly disclose the use of a Group VIII metal-containing oxidation catalyst in a dual catalyst oxidation/dehydrogenation process. The '898 patent specifically discloses the use of an oxidation catalyst comprising a Group VIII metal, a Group IVA metal, and a Group IA or IIA metal on an alumina support which has been calcined at between 900° and 1500° C. in conjunction with a dehydrogenation catalyst. The '898 patent goes on to further support the use of a dehydrogenation catalyst that is different in nature from the oxidation catalyst, and specifically a dehydrogenation catalyst comprising an alkali metalpromoted iron compound. The '237 patent discloses the use of an oxidation catalyst comprising a Group VIII metal and a second metal component selected from the group consisting of rubidium, cesium, barium, francium, and radium on a porous alumina support. This oxidation catalyst is utilized in conjunction with a dehydrogenation catalyst, and preferably a dehydrogenation catalyst again comprising an alkali metal-promoted iron compound. The '898 patent and the '237 patent both disclose the use of an oxidation catalyst similar in composition to that of the dual functional oxidation/dehydrogenation catalyst or the instant invention. However, both patents disclose the use of the oxidation catalyst in conjunction with a separate dehydrogenation catalyst and especially a dehydrogenation catalyst comprising an alkali metal-promoted iron compound.

The prior art recognizes that certain specifically formulated catalysts are useful in dehydrogenating hydrocarbons, or oxidizing with oxygen hydrogen liberated as a result of a hydrocarbon dehydrogenation reaction, or both. The catalyst of the instant invention has been described as being a useful dehydrogenation catalyst in a dehydrogenation process and a useful oxidation catalyst in an oxidation/dehydrogenation process. However, nowhere in the prior art was it intimated that the catalyst of the instant invention was useful as the sole catalyst of a selective oxidation/dehydrogenation process.

OBJECTS AND EMBODIMENTS

A principal object of the present invention is to provide an improved process for the conversion of hydrocarbons, and especially for the steam promoted oxidation/dehydrogenation of hydrocarbons. The catalyst disclosed as being useful as the dehydrogenation catalyst of the instant process has been found also to be surprisingly selective towards the oxidation of hydrogen in the presence of oxygen, hydrogen, and hydrocarbons, resulting in an increase in the yield of the desired dehydrogenated product. Accordingly, a broad embodiment of the process of the present invention is directed towards a hydrocarbon conversion process, and specifically to a process for the steam oxidation/dehydrogenation of a dehydrogenatable hydrocarbon which comprises contacting a dehydrogenatable hydrocarbon, steam, and an oxygen-containing gas in a reaction zone at conditions and in the presence of a catalyst capable of promoting both oxidation and dehydrogenation reactions. Specifically, the catalyst comprises a Group VIII noble metal component and a component selected from the group lithium, sodium, potassium, rubidium, cesium, and francium, both on a refractory inorganic oxide support. The process also entails appropriate product recycle and recovery schemes able to maximize the recovery of the desired dehydrogenated product.

In a preferred embodiment, a steam oxidation/dehydrogenation process is provided which utilizes a catalyst comprising from 0.01 to 10 wt. % platinum or palladium and 0.01 to 20 wt. % potassium, rubidium, or cesium on an alumina support having a surface area of from 5 to 120 $m^2/g$ to promote the oxidative steam dehydrogenation of a feed stream comprising an oxygen-containing gas, steam, and a $C_2-C_{30}$ dehydrogenatable hydrocarbon.

In an additional preferred embodiment, the oxidative steam dehydrogenation process is further characterized in that a dehydrogenatable hydrocarbon comprising $C_2-C_{15}$ paraffins, and steam at a steam to hydrocarbon molar ratio of from 0.1:1 to 40:1 is introduced into the first reaction zone of a reactor containing a plurality of reaction zones at conditions including a pressure from 0.1 to 10.0 atmospheres, a temperature of from 400° to 900° C., and a liquid hourly space velocity of from 0.1 to 100 $hr^{-1}$. A oxygen-containing gas is then introduced into the second, and thereafter every other reaction zone of the plurality of reaction zones such that the overall oxygen rate to all of the reaction zones ranges from 0.01 to 2 moles of oxygen per mole of $C_2-C_{15}$ paraffin. Other objects and embodiments will become evident with the following more detailed description of the invention.

BRIEF DESCRIPTION OF THE DRAWING

FIG. 1 is a graph of the oxygen conversion percentage as a function of hours on-stream. FIG. 2 is a graph of the hydrogen oxidation selectivity of the catalyst of the process as a function of hours on-stream.

DETAILED DESCRIPTION OF THE INVENTION

Figure 1:
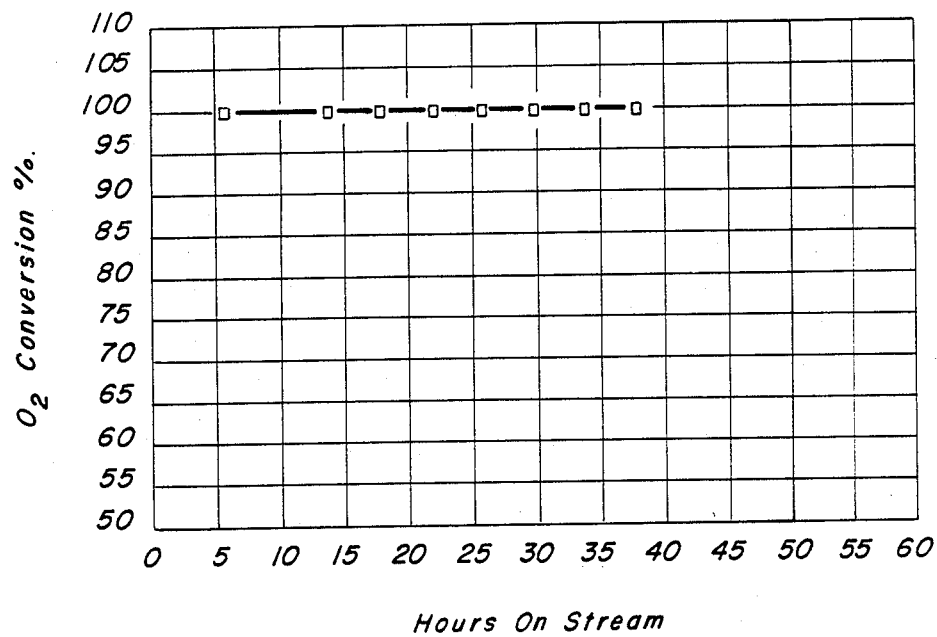
FIGS. 1 and 2 are graphical representations of the oxidation performance of the catalyst of the process of the present invention.

To summarize, the present invention is a process for the selective steam oxidation/dehydrogenation of a dehydrogenatable hydrocarbon which is accomplished utilizing a single catalyst which accomplishes both reactions. The catalyst most useful in the process of the present invention is comprised of a Group VIII noble metal component, a Group IA component, and other optional catalytic metals and modifier components, all on an inorganic substrate.

The use of a single catalyst to perform both the selective oxidation and dehydrogenation reaction in a selective steam oxidation/dehydrogenation process overcomes many of the problems inherent with a two-catalyst process where each catalyst has a single function. Specifically, the use of a single catalyst will overcome the catalyst handling problems encounterd in loading and unloading a two-catalyst system. In a two-catalyst system, the catalysts must be carefully loaded if contained in a single bed, or two or more reactors must be used when the catalyst is loaded in separate reactors. With a single catalyst, the reactor and catalyst loading become simpler and more economical. Additionally, a process using only a single catalyst is much more useful in a moving catalyst system where the catalyst is continuously being regenerated. Thus, the use of a single dual functional catalyst is an important aspect of the overall process.

As indicated above, one feature of the catalytic composite of the process of this invention is a noble metal component from Group VIII of the Periodic Table of Elements. The Group VIII noble metal may be selected from the group consisting of platinum, palladium, iridium, rhodium, osmium, ruthenium, or mixtures thereof. Platinum or palladium are, however, the preferred Group VIII noble metal components. It is believed that substantially all of the Group VIII noble metal components exists within the catalyst in the elemental metallic state.

The Group VIII noble metal component generally will comprise about 0.01 to 10 wt. %, calculated on an elemental basis, of the final catalytic composite. Preferably, the catalyst comprises about 0.1 to 5 wt. % Group VIII noble metal component, especially about 0.1 to about 5 wt. % platinum component.

The Group VIII noble metal component may be incorporated in the catalytic composite in any suitable manner such as, for example, by coprecipitation or cogelation, ion exchange or impregnation, or deposition from a vapor phase or from an atomic source or by like procedures either before, while, or after other catalytic components are incorporated. The preferred method of incorporating the Group VIII noble metal component is to impregnate the refractory oxide support with a solution or suspension of a decomposable compound of a Group VIII noble metal. For example, platinum may be added to the support by commingling the latter with an aqueous solution of chloroplatinic acid. Another acid, for example, nitric acid or other optional components may be added to the impregnating solution to further assist in dispersing or fixing the Group VIII noble metal component in the final catalyst composite. The Group VIII noble metal component may be located upon the catalyst in a variety of useful manners known in the art including uniformly dispersed, surface-impregnated or surface concentrated among others.

An alkali component, also known as a Group IA component, is also an important ingredient of the catalyst of the process of this invention. The alkali component of the present invention may be selected from the group of cesium, rubidium, potassium, sodium, lithium, or francium, or mixtures thereof. Potassium, rubidium, or cesium, or mixtures thereof, are the preferred alkali components.

Preferably, the alkali component is well dispersed through out the catalytic composite. The alkali component generally will comprise about 0.01 to 20 wt. %, calculated on an elemental basis of the final catalytic composite. The alkali component is preferably present in an amount ranging from 0.1 to 5.0 wt. % of the catalytic composite.

The alkali component may be incorporated in the catalytic composite in any suitable manner such as, for example, by coprecipitation or cogelation, by ion exchange or impregnation, or by like procedures either before, while, or after other catalytic components are incorporated into the catalyst composition. A preferred method of incorporating the preferred alkali components is to impregnate the carrier material with a solution of potassium chloride or cesium nitrate. In a most preferred embodiment, the potassium and/or cesium is present in the catalytic composite in an amount ranging from 0.1 to 1.5 wt. %.

Optional components which may be incorporated into the catalyst of the instant process include Group IIA metal components including beryllium, magnesium, calcium, strontium, and barium; and Group IIIA and IVA metal components including boron, gallium, indium, thallium, germanium, tin, and lead. A Group IVA metal is the preferred optional metal component, with tin being the most preferred optional metal component. These optional components are typically present in amounts ranging from 0.1 to 20.0 wt. %.

It is especially desired that the optional Group IVA metal component is a co-formed component. Preferably, the co-formed Group IVA component is well dispersed throughout the catalyst. The co-formed Group IVA component generally will comprise about 0.01 to 5 wt. %, calculated on an elemental basis, of the final catalyst composite. Preferably, the catalyst comprises about 0.1 to about 2 wt. % co-formed Group IVA component, especially about 0.1 to about 2 wt. % co-formed tin.

A method of incorporating a co-formed tin component into a catalyst is by cogelling it during preparation of the catalyst support. For example, a soluble tin compound such as stannous or stannic chloride may be mixed with a hydrosol. Thereafter, a gelling agent such as hexamethylenetetramine is admixed with the hydrosol and tin compound and the resulting mixture is dropped into a hot oil bath forming spheres comprising an intimate mixture of the catalyst support and tin component.

The other optional catalytic modifier components mentioned may be incorporated into the catalyst by any method known in the art such as surface impregnation or deposition, uniform impregnation or any other known distribution. Such methods include impregnation, coprecipitation, and vapor condensation among others.

A halogen component may also be incorporated into the catalyst of the instant process. Suitable halogen components include fluorine, chlorine, bromine, and iodine. The halogen component may be added to the catalyst composite during the incorporation of the carrier material with other catalyst components, for example, by using chloroplatinic acid to impregnate the platinum component. Also, the halogen component or a portion thereof may be added to the catalyst composite by contacting the catalyst with the halogen or a compound or solution containing the halogen before or after other catalyst components are incorporated with the carrier material. Suitable components containing the halogen include acids containing the halogen, for example, hydrochloric acid. Or, the halogen component or a portion thereof may be incorporated by contacting the catalyst with a compound or solution containing the halogen in a subsequent catalyst regeneration step. In the regeneration step, carbon deposited on the catalyst as coke during use of the catalyst in a hydrocarbon conversion process is burned off the catalyst and the platinum group component on the catalyst is redistributed to provide a regenerated catalyst with performance characteristics much like the fresh catalyst. The halogen component may be added during the carbon burn step or during the platinum group component redistribution step, for example, by contacting the catalyst with a hydrogen chloride gas. Also, the halogen component may be added to the catalyst composite by adding the halogen or a compound or solution containing the halogen, such as propylene dichloride, for example, to the hydrocarbon feed stream or to the recycle gas during operation of the hydrocarbon conversion process.

The inorganic oxide carrier material useful for the catalyst of this process may be any carrier material known which is useful as a catalytic support. However, alumina is the most preferred support material. The most preferred inorganic oxide support of the present invention is alumina having a surface area of from 1 to 500 $m^2/g$, and preferably from 5 to 120 $m^2/g$. The alumina carrier material may be prepared in any suitable manner from synthetic or naturally occurring raw materials. The carrier may be formed in any desired shape such as spheres, pills, cakes, extrudates, powders, granules, etc., and it may be utilized in any particle size. A preferred shape of alumina is the sphere. A preferred particle size is about 1/16-inch in diameter, though particles as small as about 1/32-inch, and smaller, may also be utilized, as well as particles larger than 1/16-inch diameter.

In a most preferred method, the alumina is in the form of spheres. To make alumina spheres, aluminum metal is converted into an alumina sol by reacting it with a suitable peptizing acid and water, and then dropping a mixture of the sol, and a gelling agent into a hot oil bath. The mixture forms spherical particles of an alumina gel in the hot oil bath which are easily converted into the preferred gamma- or eta-alumina carrier material by known methods including aging, drying, and calcining. Other shapes of the alumina carrier material may also be prepared by conventional methods. A Group IVA metal component as previously mentioned may be added to the alumina sol or alumina carrier material prior to substrate formation.

The preferred alumina support having a surface area of between 5 and 120 m$^2$/g of the present invention may be prepared by subjecting a precalcined alumina support to an additional calcination step. As indicated heretofore, in preparing an alumina support, the support is typically calcined and dried. However, it has been discovered that the novel pore distribution of the preferred catalyst of the present invention may be induced by a calcination step performed subsequent to the initial calcination. Accordingly, an alumina support optionally containing a co-formed Group IVA metal component is subjected to a calcination step conducted at from about 800° to about 1200° C. The calcination may be conducted in air, steam, or a mixture thereof. When a mixture is employed, generally the steam will comprise from 1% to 50%.

The catalyst previously described as useful in the process of the instant invention is very useful in both the dehydrogenation of dehydrogenatable hydrocarbons in the presence of steam, and also in the selective oxidation of hydrogen produced by the dehydrogenation reaction. Any dehydrogenatable hydrocarbon may be utilized as feed to the present invention. However, it is preferred that the hydrocarbons which may be dehydrogenated include dehydrogenatable hydrocarbons having from 2 to 30 or more carbon atoms including paraffins, alkylaromatics, naphthenes, and olefins. One group of hydrocarbons which can be dehydrogenated with the catalyst is the group of paraffins having from 2 to 30 or more carbon atoms. The catalyst is particularly useful for dehydrogenating paraffins having from 2 to 15 or more carbon atoms to the corresponding monoolefins or for dehydrogenating monoolefins having from 2 to 15 or more carbon atoms to the corresponding diolefins or acetylene derivatives. The catalyst is especially useful in the dehydrogenation of $C_2$–$C_6$ paraffins into monoolefins.

The dehydrogenation of a dehydrogenatable hydrocarbon such as, for example, those mentioned above, is effected in the instant process by contacting the dehydrogenatable hydrocarbon and steam, with the previously described catalyst at conditions useful for both the steam dehydrogenation of hydrocarbons and the selective oxidation of hydrogen. Such conditions comprise temperatures which range from about 400° to about 900° C., and a reaction pressure in the range of from about 0.1 to about 10 atmospheres; the exact dehydrogenation conditions are, however, a function of the particular dehydrogenatable hydrocarbon undergoing dehydrogenation. Other reaction conditions will include a liquid hourly space velocity based on the hydrocarbon charge of from about 0.1 to about 100 hr$^{-1}$ and steam to hydrocarbon molar ratios ranging from about 0.1:1 to about 40:1.

The dehydrogenation of hydrocarbons is an endothermic process. In a system employing a dehydrogenation catalyst only, it is typically necessary to add superheated steam at various points in the process or to intermittently remove and reheat the reaction stream between catalyst beds. In an improvement, processes were developed which utilized a two-catalyst system with distinct beds or reactors of dehydrogenation or selective oxidation catalysts. The purpose of the selective oxidation catalysts was to selectively oxidize the hydrogen produced as a result of the dehydrogenation reaction with oxygen that had been added to the oxidation zone to generate heat internally in the process. The heat generated would typically be sufficient to cause the reaction mixture to reach desired dehydrogenation temperatures for the next dehydrogenation step. The instant invention is an improvement of this previously mentioned system. As has been previously mentioned, in this invention, one specific catalyst can be used to accomplish both the dehydrogenation and oxidation reactions. Before explaining the preferred reactor configurations, more details of the oxidation aspect of the invention are disclosed.

The selective oxidation step of this process utilizes the hydrogen which has been produced in the dehydrogenation step of the process to supply heat to the next dehydrogenation reaction section. To accomplish this, an oxygen-containing gas is first introduced into the reactor, preferably at a point adjacent to the selective oxidative catalyst section. The oxygen in the oxygen-containing gas is necessary to oxidize the hydrogen contained in the reaction stream. Examples of oxygen-containing gases which may be utilized to effect the selective oxidation of the hydrogen which is present will include air, oxygen, or air or oxygen diluted with other gases such as steam, carbon dioxide and inert gases such as nitrogen, argon, helium, etc. The amount of oxygen which is introduced to contact the process stream may range from about 0.01:1 to about 2:1 moles of oxygen per mole of hydrogen contained in the process stream at the point where oxygen is added to the process stream. In the selective oxidation reaction, the process stream which comprises unreacted dehydrogenatable hydrocarbon, dehydrogenated hydrocarbon, and hydrogen is reacted with oxygen in the presence of the selective steam oxidation/dehydrogenation catalyst whereby hydrogen is selectively oxidized to produce water with very little of the oxygen reacting with the process stream hydrocarbons.

The oxygen-containing reactant may be added to the instant process in various ways such as by admixing oxygen with a relatively cool hydrocarbon feed stream or with the steam diluent, or it may be added directly to the reactor independently of the feed hydrocarbons or the steam diluent. In addition, the oxygen-containing reactant can be added at one or more points in the reactor in such a fashion as to minimize local concentrations of oxygen relative to hydrogen in order to distribute the beneficial temperature rise produced by the selective hydrogen oxidation over the entire length of the reaction zone. In fact, using a plurality of injection points for introducing the oxygen-containing gas into the steam oxidation/dehydrogenation reaction zone is a preferred mode of operation for the instant process. This procedure minimizes the opportunity for local build-up of the concentration of oxygen relative to the amount of hydrogen, thereby minimizing the opportunity for undesired reaction of the oxygen-containing gas with either feed or product hydrocarbons.

It is also an aspect of this invention that hydrogen may be a co-feed of the process. Hydrogen if needed would typically be injected into the oxidation section of the steam oxidation/dehydration process. The hydrogen would be added as fuel, so to speak, to elevate the temperature of the process stream. The hydrogen could be added to the inlet of the reactor with the oxygen-containing gas to elevate the temperature of the feed stream to dehydrogenation reaction conditions, or anywhere desired and effective in the reaction zone.

According to the unique process of the present invention, a mixture of dehydrogenatable hydrocarbons, steam, and an oxygen-containing gas is contacted with the catalytic composite of the present invention in a steam oxidation/dehydrogenation reaction zone maintained at steam oxidation/dehydrogenation conditions. This contacting step may be accomplished by using the catalyst in a fixed bed system, a moving bed system, a fluidized bed system, or in a batch type operation. However, in view of the fact that the attrition losses of the valuable catalyst should be minimized and of the well known operational advantages, it is preferred to use either a fixed bed catalytic system, or a dense phase moving bed system such as is shown in U.S. Pat. No. 3,725,249.

If a fixed bed catalytic reaction system is used for the process of the present invention, it is anticipated that the reaction system could take many forms. The first possibility is that the reaction would comprise a single reaction zone within a single reactor with single inlet and outlet ports. All co-feeds would enter the inlet of the reactor and products and by-products would leave the system through the reactor outlet port.

A permeation of this flowscheme would be to have a reaction zone having one or more oxygen-containing gas inlet ports separate from the inlet or outlet ports so that oxygen could be injected at different points into the catalyst bed of the reaction zone. This type of configuration would mimic a reaction system with a plurality of catalyst beds only in this instance, it would be a single reaction zone in which the oxidation and dehydrogenation function of the catalysts was dispersed throughout the bed in a plurality of locations.

Of course, the catalyst could be distributed in a plurality of distinct reactors each having a specific function, either steam dehydrogenation or oxidation, or the fixed bed reactor system could comprise a combination of the two possibilities. The choice of the best system would likely depend upon many factors including available equipment, particular reaction speed, and efficiency, as well as optimum reaction conditions for the two distinct reactions being performed. Regardless of the fixed bed catalyst system employed, the hydrocarbon may be contacted with the catalyst bed in either upward, downward, or radial flow fashion. Radial flow of the hydrocarbon through the catalyst bed is preferred for commercial scale reactors. The hydrocarbon must be in the vapor phase when it contacts the catalyst.

It should be noted that in a fixed bed reaction system that there are two functions the catalyst is performing in different areas of the catalyst beds. Of course, these two catalytic functions are steam dehydrogenation and selective oxidation. The distinct areas where these reactions occur are referred to herein as reaction zones. These reaction zones may be distinct, wherein a mechanical means is present which separates a volume of catalyst which is used to dehydrogenate the reaction mixtures from a volume of catalyst that is used to selectively oxidize hydrogen. On the other hand, these zones may be indistinct where there is no physical means used to separate the reaction zones. In either situation, the function the catalyst is performing will effectively separate the reaction zones. Where there are distinct reaction zones within the steam oxidation/dehydrogenation reaction zone, it is preferable that every other reaction zone of a plurality of reaction zones performs the same catalytic function. That is to say, if the first reaction zone is used to dehydrogenate the hydrocarbon, then the second zone is used for selective oxidation, the third zone for dehydrogenation, the fourth zone for oxidation, and so on. The same holds true if the first reaction zone of a plurality of reaction zones is used to selectively oxidize hydrogen. This description holds true for a process of the instant invention which employs a moving bed of catalyst also.

The process of the instant invention can best be accomplished in a moving bed catalytic system. Such a system is described in U.S. Pat. No. 3,725,249 and is most useful for use in a reaction where the catalyst becomes deactivated by coke deposition thereon. In such a situation, the catalyst of the instant process would continuously move through the plurality of reaction zones of the process and once deactivated, be transported to a continuous catalyst regeneration system. Once regenerated, the catalyst would be returned to the reaction system.

It is an aspect of this invention that the selective steam oxidation/dehydrogenation conversion process be a complete process. That is to say, the process will comprise a reaction section and other sections such as gas recycle, liquid recycle, product recovery, and the like such that the process is viable and efficient. Examples of some of the product recovery techniques that could be employed alone or in combination in the product recovery zone of a hydrocarbon conversion process are: distillation including vacuum, atmospheric, and superatmospheric distillation; extraction techniques including, for example, liquid/liquid extractions, vapor/liquid extractions, supercritical extractions and others; absorption techniques, adsorption techniques, and any other known mass transfer techniques which can achieve the recovery of the desired products.

The following examples are introduced to further describe the catalyst and process of the invention. The examples are intended as illustrative embodiments and should not be considered to restrict the otherwise broad interpretation of the invention as set forth in the claims appended hereto.

EXAMPLE I

Precalcined spheroidal theta-alumina particles having 0.5 wt. % tin and an average surface area of approximately 86 $m^2/g$ and averaging about 1/16-inch in diameter were consecutively impregnated with 0.75 wt. % platinum and 3.5 wt. % cesium. Precalcination of the alumina spheres was effected in flowing air at a temperature of about 1080° C. over about a 3-hour interval. Impregnation was accomplished with a chloroplatinic acid solution in a rotary steam evaporator or dryer, while evaporating the solution to dryness. The platinum-impregnated spheres were subsequently calcined in air containing 10% steam for 2 hours at about 570° C. The calcined, platinum-impregnated spheres were next impregnated with cesium from an aqueous solution of cesium nitrate and further calcined in air for about 3 hours at 566° C. followed by reduction with hydrogenation at 566° C. for 2 hours. The resulting catalytic composition is hereinafter referred to as Catalyst A.

EXAMPLE II

A catalyst support comprising alumina and a tin component was prepared by means of cogelation. This support was calcined at a temperature of about 677° C. for about 1.5 hours. Thereafter, using the same impregnation method as that described in Example I, a catalyst was prepared utilizing this support. The resulting catalyst was designated Catalyst B. Catalyst B comprised about 0.75 wt. % platinum, about 4.4 wt. % cesium, and about 0.5 wt. % tin. The catalyst support had a surface area of 180 $m^2/g$.

EXAMPLE III

In this example, a catalyst was prepared substantially as set forth above. However, in this case, the catalyst support comprising a cogelled Group IVA metal component and alumina was subjected to a second calcination step for about 2.5 hours. The first calcination step was accomplished at 677° C. This second calcination step was effected at a temperature of about 1080° C. in a muffle furnace for 3 hours. Following the second calcination step, the support was impregnated substantially as in Example I above.

This catalyst was designated Catalyst C. Catalyst C comprised about 0.70 wt. % platinum, about 3.86 wt. % cesium, about 0.50 wt. % tin. Catalyst C had a surface area of about 85 $m^2/g$.

EXAMPLE IV

In this example, two catalysts were prepared as set forth in Example III except that the catalyst was impregnated with a potassium component instead of a cesium component. Catalyst D, comprising a low surface area tin-containing alumina base, was impregnated with platinum and potassium such that Catalyst D comprised 0.76 wt. % platinum, 1.31 wt. % potassium, and 0.50 wt. % tin.

Catalyst E was prepared from essentially the same base and was impregnated with platinum and potassium such that Catalyst E comprised 0.75 wt. % platinum, 2.70 wt. % potassium, and 0.50 wt. % tin.

EXAMPLE V

In this example, Catalyst A was evaluated in a first test as a dehydrogenation catalyst, and in a second test as an oxidation/dehydrogenation catalyst. These comparison tests were carried out in a pilot plant comprising two reactors in series, and product separation facilities. All feed components were introduced into the inlet of the first reactor. All operating variables were kept constant between tests except that the first reactor feed temperature was lower in the second test so that the feed to the second reactor could be heated by selective hydrogen oxidation to the second reactor feed temperature. A detailed comparison of the operating variables is found in Table 1 below.

TABLE 1

| Variable | (Test 1) Dehydrogenation | | (Test 2) Oxidation/Dehydrogenation | |
|---|---|---|---|---|
| | Reactor #1 | Reactor #2 | Reactor #1 | Reactor #2 |
| Reaction | Dehydrogenation | Dehydrogenation | Selective Oxidation | Dehydrogenation |
| Gas Injection | $N_2$ | — | Air | — |
| Inlet Temp, °C. | 600 | 600 | 540 | 600 |
| Maximum Temp, °C. | 600 | — | 600 | — |
| LHSV, $hr^{-1}$ | 80 | 8 | 80 | 8 |
| Outlet Pres., atm | 1.7 | 1.4 | 1.7 | 1.4 |
| Feed, mole/hr | | | | |
| $H_2O$ | 2.07 | | 2.0 | |
| $C_3$ | 0.7 | | 0.7 | |
| $C_3=$ | 0.3 | | 0.3 | |
| $H_2$ | 0.3 | | 0.3 | |
| $N_2$ | 0.13 | | — | |
| Air | — | | 0.16 | |

Pilot plant test 2 was designed to model a first oxidation reaction zone and a second dehydrogenation reaction zone. That is to say, the feedstock for both tests mimics a dehydrogenation reaction zone intermediate product. Additionally, nitrogen was added to the first, dehydrogenation only, test to maintain the reactor space velocities. The second test used air to maintain these space velocities and to promote hydrogen oxidation.

The following Tables 2 and 3 contain information about the pilot plant results of both tests.

TABLE 2

| | Propane Conversion (Mole %) | | | |
|---|---|---|---|---|
| | Test #1 | | Test #2 | |
| Hours On-Stream | Rx #1 Out | Rx #2 Out | Rx #1 Out | Rx #2 Out |
| 2 | 0.5 | — | 0.5 | 15.0 |
| 6 | 3.5 | 14.5 | 2.5 | 16.0 |
| 10 | 3.0 | 13.0 | 1.5 | 13.7 |
| 14 | 2.5 | 11.5 | 1.4 | 11.5 |
| 18 | 2.5 | 11.0 | 1.0 | 11.5 |
| 22 | 2.4 | 9.5 | 0.8 | 10.8 |
| 26 | 2.0 | 9.2 | 0.2 | 10.0 |
| 30 | 1.9 | 8.5 | 0.5 | 9.1 |
| 34 | 1.5 | 7.6 | 0.4 | 8.3 |
| 38 | 2.0 | 6.9 | 0.2 | 7.4 |

TABLE 3

| | Selectivity to Propylene (Mole %) | | | |
|---|---|---|---|---|
| | Test #1 | | Test #2 | |
| Hours On-Stream | Rx #1 Out | Rx #2 Out | Rx #1 Out | Rx #2 Out |
| 2 | — | 98.6 | 100 | 98.5 |
| 6 | 98.0 | 96.4 | — | 97.0 |
| 10 | 97.5 | 96.0 | 100 | 96.2 |
| 14 | 98.0 | 96.1 | 100 | 96.3 |
| 18 | 97.5 | 96.0 | 100 | 96.0 |
| 22 | 97.3 | 95.6 | 100 | 95.5 |
| 26 | 97.0 | 95.6 | 100 | 95.5 |
| 30 | 96.4 | 96.1 | 100 | 95.0 |
| 34 | 96.2 | 96.0 | 100 | 94.6 |
| 38 | 95.6 | 94.9 | 100 | 95.5 |

A review of the dehydrogenation results of the two tests indicates that the results are similar for both tests. The propane conversion (at Reactor #2 outlet) is almost identical for both tests with the propane conversion for the oxidation/dehydrogenation Test 2 being slightly better than Test 1 overall. The first reactor outlet conversion is generally lower in the oxidation case in Test 2 than in comparison to the dehydrogenation case in Test 1 because the average temperature is lower in the first reactor of the second test.

The propylene selectivity data (that is the percent of the converted product that is propylene) indicates that the selectivity is similar for the reactor #2 in both tests. This is evidenced by comparing the reactor #2 outlet selectivity data for Tests 1 and 2. The reactor #1 outlet selectivity is higher in Test 1 than Test 2.

Figure 2:
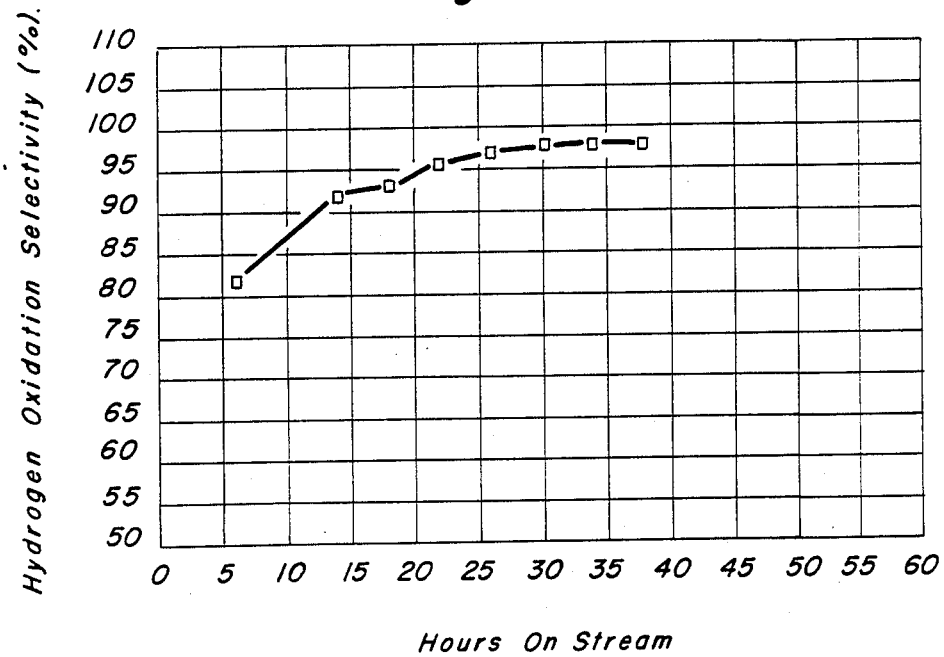

FIGS. 1 and 2 represent the oxidation zone performance of the catalyst of reactor 1 in the second test. FIG. 1 represents the oxygen ($O_2$) conversion (the percent of the oxygen converted to another form) versus time-on-stream. FIG. 1 indicates that $O_2$ is totally oxidized in the oxidation zone during the test period. FIG. 2 represents the selectivity of the oxygen to desirably combust hydrogen, that is, the amount of oxygen converted that oxidizes hydrogen. From FIG. 2, it can be seen that the desirable hydrogen oxidation selectivity of the selective steam oxidation/dehydrogenation catalyst of the instant process is high at 83% and increases further to a very acceptable value of 98%. The catalyst of the process of the instant invention is therefore a very efficient oxidation catalyst as it completely oxidized all added oxygen while maximizing hydrogen oxidation, thus minimizing the combustion of valuable hydrocarbons with the oxygen. Overall the process produces a dehydrogenated product in greater amounts with a single catalyst than does a single catalyst-containing dehydrogenation process of the prior art.

EXAMPLE VI

Catalyst B having a surface area of 180 m²/g and Catalyst C having a surface area of 85 m²/g as prepared in Examples II and III, respectively, were evaluated in pilot plant testing to determine the effect of catalyst base surface area on catalyst performance. Both catalysts were tested under steam dehydrogenation conditions including a temperature of 600° C., a pressure of 2.0 atm, a $H_2O$/propane steam molar ratio of 2, and a liquid hourly space velocity (LHSV) of 3 hr$^{-1}$. Propane, as mentioned above, is the hydrocarbon to be dehydrogenated.

The conversion and selectivity of the dehydrogenation tests are indicated in Table 4 below.

TABLE 4

| Hours On-Stream | Propylene Selectivity (mole %) | | Propane Conversion (%) | |
|---|---|---|---|---|
| | Catalyst B | Catalyst C | Catalyst B | Catalyst C |
| 10 | 91.0 | 95.1 | 21 | 33 |
| 20 | 92.5 | 95.0 | 21 | 32 |
| 30 | 96.2 | 96.2 | 21 | 34 |
| 40 | 91.1 | 97.0 | 15 | 35 |
| 50 | 88.0 | 95.4 | 10 | 35 |
| 60 | 87.2 | 95.4 | 7 | 35 |

It is very evident from Table 4 that Catalyst C with a lower surface area (85 m²/g) than Catalyst B (180 m²/g) is the superior dehydrogenation catalyst. This is felt to be a result of the reduced surface area of Catalyst C. Both the propane conversion (the percent of the propane converted to other products) and propylene selectivity (the percent of the converted products that are propylene) of Catalyst C are superior to those of Catalyst B. Thus, a catalyst with a lower surface area is more effective in accomplishing the dehydrogenation aspect of the selective steam oxidation/dehydrogenation catalyst of the instant invention.

EXAMPLE VII

Catalysts C, D, and E were tested at dehydrogenation conditions to determine the effects of cesium in comparison to potassium on the dehydrogenation function of the selective steam oxidation/dehydrogenation catalyst. The effects on the dehydrogenation of propane using catalysts containing two levels of potassium was also studied. Table 5 below compares the composition of each catalyst.

TABLE 5

| Variable | Catalyst C | Catalyst D | Catalyst E |
|---|---|---|---|
| Surface Area, m²/g | 85 | 85 | 85 |
| Pt, wt. % | 0.72 | 0.76 | 0.75 |
| Sn, wt. % | 0.5 | 0.5 | 0.5 |
| Cs, wt. % | 3.86 | 0 | 0 |
| K, wt. % | 0 | 1.31 | 2.70 |

All three catalysts were tested for their ability to dehydrogenate propane under pilot conditions including a temperature of 600° C., a pressure of 2 atmospheres, a $H_2O$/propane steam molar feed ratio of 2, and a liquid hourly space velocity (LHSV) of 3 hr$^{-1}$. The conversion of propane for each catalyst is detailed below in Table 6.

TABLE 6

| | Propane Conversion (%) | | |
|---|---|---|---|
| Hours On-Stream | Catalyst C | Catalyst D | Catalyst E |
| 10 | 33 | 41 | 5 |
| 20 | 32 | 40 | 10 |
| 30 | 34 | 39 | 14 |
| 40 | 35 | 38 | 14 |
| 50 | 35 | 37 | 14 |
| 60 | 35 | 36 | 14 |

TABLE 7

| | Propane Selectivity (mole %) | | |
|---|---|---|---|
| Hours On-Stream | Catalyst C | Catalyst D | Catalyst E |
| 10 | 95.0 | 94.5 | — |
| 20 | 95.6 | 94.5 | 85.0 |
| 30 | 96.0 | 94.3 | 86.7 |
| 40 | 96.2 | 94.5 | 87.0 |
| 50 | 95.7 | 94.5 | 87.0 |

TABLE 7-continued

| | Propane Selectivity (mole %) | | |
|---|---|---|---|
| Hours On-Stream | Catalyst C | Catalyst D | Catalyst E |
| 60 | 96.0 | 94.4 | 87.0 |

The data presented in Table 6 indicates that both the cesiumcontaining catalyst, Catalyst C, and the potassium-containing Catalyst D, are both about equally efficient in promoting the dehydrogenation of propane into propylene. The data also indicates that a potassium-containing catalyst with a low potassium level (Catalyst D) is much more efficient in the dehydrogenation of propane than a catalyst (Catalyst E) containing higher levels of potassium.

The data presented in Table 7 again shows that the cesiumcontaining catalyst, Catalyst C, and the low potassium-containing catalyst, Catalyst D, exhibit selectivity performance of about 95 mole %. This is much better than the 87 mole % selectivity of the high potassium-containing catalyst, Catalyst E.

What is claimed is:

1. A process for the steam dehydrogenation of a dehydrogenatable hydrocarbon with oxidative reheating which comprises contacting a $C_2$-$C_{30}$ dehydrogenatable hydrocarbon, steam, and an oxygen-containing gas in a reaction zone at conditions sufficient to promote both oxidation and dehydrogenation reactions with a catalyst comprising a Group VIII noble metal component, one or more components selected from the group lithium, potassium, rubidium, cesium, and francium, and a component selected from the group consisting of boron, gallium, indium, germanium, tin, and lead, all on an inorganic oxide support, and recovering the products of the reaction.

2. The process of claim 1 further characterized in that the dehydrogenatable hydrocarbon comprises $C_2$-$C_{15}$ paraffins.

3. The process of claim 1 further characterized in that the Group VIII noble metal is platinum or palladium.

4. The process of claim 3 further characterized in that the Group VIII noble metal is platinum.

5. The process of claim 1 further characterized in that the catalyst component selected from the group comprising lithium, sodium, potassium, rubidium, cesium, or francium is cesium or potassium or a mixture thereof.

6. The process of claim 5 further characterized in that the catalyst component selected from cesium or potassium or mixtures thereof is potassium.

7. The process of claim 6 further characterized in that the potassium is present in the catalyst in an amount ranging from 0.01 to 20.0 wt. %.

8. The process of claim 1 further characterized in that the catalyst comprises a halogen component.

9. The process of claim 1 further characterized in that the component selected from the group comprising boron, gallium, indium, thallium, germanium, tin, and lead is tin.

10. The process of claim 1 further characterized in that the catalyst comprises a Group IIA component.

11. The process of claim 1 further characterized in that the inorganic oxide support is alumina having a surface area of from 1 to 500 $m^2/g$.

12. A process for the steam dehydrogenation of a dehydrogenatable hydrocarbon with oxidative reheating which comprises contacting a $C_2$-$C_{30}$ dehydrogenatable hydrocarbon, steam, and an oxygen-containing gas in a reaction zone at conditions sufficient to promote both oxidation and dehydrogenation reactions with a catalyst comprising from 0.1 to 10 wt. % platinum or palladium, 0.01 to 20 wt. % potassium, rubidium, or cesium, or a mixture thereof, and a 0.01 to 5.0 wt. % tin on an alumina support having a surface area of from 5 to 120 $m^2/g$, and recovering the products of the reaction.

13. The process of claim 12 further characterized in that the reaction zone is configured such that the $C_2$-$C_{30}$ dehydrogenatable hydrocarbon, steam, and the oxygen-containing gas are all introduced into the inlet of a single bed of catalyst.

14. The process of claim 13 further characterized in that hydrogen is a co-feed.

15. The process of claim 12 further characterized in that the $C_2$-$C_{30}$ dehydrogenatable hydrocarbons and steam are introduced into the inlet of the reaction zone containing a single catalyst bed in the absence of oxygen while an oxygen-containing gas is introduced at an intermediate point of the single catalyst bed of the reaction zone.

16. The process of claim 12 further characterized in that the reaction zone contains a plurality of reaction zones and that the $C_2$-$C_{30}$ dehydrogenatable hydrocarbon and steam are introduced into the first of the plurality of reaction zones and an oxygen-containing gas is introduced into the second and every other reaction zone of the plurality of reaction zones.

17. The process of claim 16 further characterized in that plurality of reaction zones contain fixed beds of catalyst.

18. The process of claim 16 further characterized in that the plurality of reaction zones contain a moving bed of catalyst.

19. A process for the steam dehydrogenation of a dehydrogenatable hydrocarbon with oxidative reheating which comprises contacting a dehydrogenatable hydrocarbon comprising $C_2$-$C_{15}$ paraffins and a steam at a steam to hydrocarbon molar ratio of from 0.1:1 to 40:1, at a pressure from 0.1 to 10 atmospheres, a temperature of from 400° to 900° C., and a liquid hourly space velocity (LHSV) of from 0.1 to 100 $hr^{-1}$ with a catalyst in the first reaction zone of a reactor containing a plurality of reaction zones and introducing an oxygen-containing gas into the second, and every other reaction zone of the plurality of reaction zones such that the total rate of the oxygen-containing gas introduced into the reaction zone ranges from 0.01 to 2 moles of oxygen per mole of $C_2$-$C_{15}$ paraffin feed wherein the catalyst is comprised of from 0.1 to 5 wt. % platinum, and from 0.01 to 5 wt. % potassium or cesium or mixtures thereof on an alumina support having a surface area of from 5 to 120 $m^2/g$ and recovering the products of the reaction.

20. The process of claim 19 further characterized in that the plurality of reaction zones contain fixed beds of catalysts.

21. The process of claim 19 further characterized in that the plurality of reaction zones contain moving beds of catalyst.

22. The process of claim 19 further characterized in that the dehydrogenatable hydrocarbon is a $C_2$-$C_6$ paraffin.

23. The process of claim 19 further characterized in that the catalyst contains a tin component.

24. The process of claim 21 further characterized in that the potassium or cesium component comprises potassium in an amount ranging from 0.1 to 1.5 wt. %.

* * * * *